United States Patent [19]
Dion

[11] Patent Number: 5,913,867
[45] Date of Patent: Jun. 22, 1999

[54] SURGICAL INSTRUMENT

[75] Inventor: Ernest A. Dion, Danvers, Mass.

[73] Assignee: Smith & Nephew, Inc., Memphis, Tenn.

[21] Appl. No.: 08/772,340

[22] Filed: Dec. 23, 1996

[51] Int. Cl.⁶ .................................................. A61B 17/14
[52] U.S. Cl. ............................ 606/180; 606/80; 606/170
[58] Field of Search ............................. 604/22; 606/170, 606/180, 80

[56] References Cited

U.S. PATENT DOCUMENTS

| | | |
|---|---|---|
| 2,369,925 | 2/1945 | Smith . |
| 3,584,629 | 6/1971 | Hoef et al. . |
| 3,937,222 | 2/1976 | Banko . |
| 3,976,077 | 8/1976 | Kerfoot . |
| 4,203,444 | 5/1980 | Bonnell et al. . |
| 4,274,414 | 6/1981 | Johnson et al. . |
| 4,320,761 | 3/1982 | Haddad . |
| 4,445,509 | 5/1984 | Auth . |
| 4,646,738 | 3/1987 | Trott . |
| 4,834,729 | 5/1989 | Sjostrom . |
| 4,842,578 | 6/1989 | Johnson et al. . |
| 4,983,179 | 1/1991 | Sjostrom . |
| 5,228,459 | 7/1993 | Caspari et al. . |
| 5,269,785 | 12/1993 | Bonutti et al. . |
| 5,269,794 | 12/1993 | Rexroth .................................. 606/80 |
| 5,286,253 | 2/1994 | Fucci ...................................... 606/170 |
| 5,320,635 | 6/1994 | Smith . |
| 5,322,505 | 6/1994 | Krause et al. . |
| 5,366,468 | 11/1994 | Fucci et al. . |
| 5,437,630 | 8/1995 | Daniel et al. . |
| 5,456,689 | 10/1995 | Kresch et al. ............................ 604/22 |
| 5,489,291 | 2/1996 | Wiley . |
| 5,618,293 | 4/1997 | Sample et al. ........................ 606/180 |
| 5,690,660 | 11/1997 | Kauker et al. ......................... 606/170 |

FOREIGN PATENT DOCUMENTS

| | | |
|---|---|---|
| 296 16 633 U | 12/1989 | Germany . |
| 596229 | 3/1978 | U.S.S.R. . |
| 623551 | 8/1978 | U.S.S.R. . |
| 762870 | 9/1980 | U.S.S.R. . |
| 2087239 | 5/1982 | United Kingdom . |
| WO 96 12453 | of 1996 | WIPO . |

OTHER PUBLICATIONS

Smith & Nephew Endoscopy Inc. TurboCutter Instrument (Part No. 3449).

Aesculap®, Aesculap® Arthroscopy System, product literature, including GB 616 Reamer (p. 13).

English Abstract of DE 39 06 301 A, Germany.

*Primary Examiner*—Michael Buiz
*Assistant Examiner*—Julian W. Woo
*Attorney, Agent, or Firm*—Fish & Richardson P.C.

[57] ABSTRACT

A surgical instrument comprises an inner tube which rotates within an outer tube and carries a surgical tool that includes a burr for cutting tissue exposed to the burr through an opening in the outer tube. The instrument includes several features which enhance the efficiency at which tissue fragments severed by the burr are aspirated through the inner tube, and which enable the burr to effectively cut relatively soft tissue as well as harder tissue such as bone. For example, the burr includes a proximal shank having a wall that has an aperture therein with a substantial width relative to an outer diameter of the wall for conveying tissue fragments cut by the burr into an interior chamber of the shank, and thence into a passage in the inner tube. The opening in the outer tube is axially elongated sufficiently to expose a major portion of the aperture. The large aperture and its exposure by the outer tube opening reduce the risk of clogging by admitting larger tissue fragments into the inner tube for aspiration. Additionally, the burr includes a plurality of grooves that are axially elongated and inclined transversely to the flutes, and the grooves define a plurality of axially spaced notches in each of the cutting edges. The notches divide the cutting edges into relatively small segments that produce correspondingly small tissue fragments (even when the burr is used to cut soft tissue) to further reduce the risk of clogging. In addition, the cutting edges are preferably provided with a positive rake that makes the cutting edges sharper and suitable for effectively cutting, rather than tearing or shredding, relatively soft tissue.

27 Claims, 4 Drawing Sheets

FIG. 9

SURGICAL INSTRUMENT

BACKGROUND

This invention relates to endoscopic surgical instruments, and in particular to powered endoscopic surgical instruments for, e.g., arthroscopy.

Powered endoscopic surgical instruments typically include a stationary outer tube within which an inner tube that carries a surgical tool on its distal end is rotated by a motor. Body tissue exposed to the surgical tool through an opening in the outer tube is cut by the rotating tool. Tissue fragments cut by the tool and irrigating fluid from the surgical site are drawn through an interior suction passage in the inner tube in response to suction applied at the proximal end of the instrument. Several such surgical instruments are described in U.S. Pat. Nos. 4,203,444, 4,274,414, 4,834,729, 4,842,578, 4,983,179, and 5,322,505, all of which are assigned to the assignee of the present invention and incorporated herein by reference.

The configuration of the surgical tool is typically a function of the type of body tissue to be cut. For example, in instruments for cutting relatively soft tissue (such as cartilage and synovial tissue), the tool is a blade formed by sharpened edges of a window in the inner tube which cooperates with sharpened edges of the outer tube opening as the inner tube rotates. In an "abrader" for sculpting bone tissue, the surgical tool is a solid, fluted burr the proximal shank of which is mounted on the inner tube. The burr includes a series of axially elongated, inclined cutting edges spaced circumferentially around the burr by the flutes. A slot in the burr shank conveys bone fragments cut by the burr and irrigation fluid into the interior passage of the inner tube for removal by the applied suction.

SUMMARY

This invention features a surgical instrument of the kind in which an inner tube rotates within an outer tube and carries a surgical tool that includes a burr for cutting tissue exposed to the burr through an opening in the outer tube. The invention provides several features which enhance the efficiency at which tissue fragments severed by the burr are aspirated through the inner tube, and which enable the burr to effectively cut relatively soft tissue as well as harder tissue such as bone.

In one general aspect of the invention, the burr includes a proximal shank having a wall that has an aperture therein with a substantial width relative to an outer diameter of the wall for conveying tissue fragments cut by the burr into an interior chamber of the shank, and thence into a passage in the inner tube.

Preferred embodiments may include one or more of the following features.

The width of the aperture is approximately one-half of the diameter of a wall of the shank. More preferably, the aperture width is greater than one-half of the wall diameter. A portion of the wall disposed adjacent to a distal end of the aperture includes an inclined surface that slopes proximally toward the aperture. The inclined surface is oriented at an acute angle to a pair of planar axial surfaces of the wall that define the sides of the aperture. The shank wall is tubular so that its interior chamber is substantially cylindrical.

The large aperture in the shank admits even large tissue fragments, thereby reducing the risk of clogging and enhancing the fluid flow rate supported by the instrument. The inclined surface serves as a ramp which helps guide tissue fragments into the aperture for more efficient aspiration.

The burr includes a plurality of cutting edges circumferentially spaced by a plurality of flutes disposed in an exterior surface of the surgical tool, and at least one of the cutting edges includes at least one notch therein. Preferably, a plurality of axially spaced notches are provided in the cutting edge. More preferably, the axially spaced notches are provided in each one of the cutting edges. The cutting edges and the flutes are axially elongated and are inclined relative to a longitudinal axis of the burr.

In another general aspect of the invention, the opening in the outer tube is axially elongated sufficiently to expose a major portion of the aperture.

Preferred embodiments may include one or more of the following features.

The elongation of the outer tube opening is such that the proximal end of the opening is disposed adjacent to, and more preferably, proximally of, a proximal end of the aperture. The axially elongated opening exposes the burr to tissue along one side of the burr, and defines a hood in the outer tube for the opposite side of the burr. Because most, if not all, of the aperture is directly exposed to the tissue by the outer tube opening, tissue fragments more easily enter the aperture (and hence the suction passage) than if the fragments were required to travel proximally between the inner and outer tubes before reaching the aperture. This further reduces the risk of clogging and enhances aspiration efficiency.

In another general aspect of the invention, the burr includes a plurality of grooves that are axially elongated and inclined transversely to the flutes, and the grooves define a plurality of axially spaced notches in each of the cutting edges.

Preferred embodiments may include one or more of the following features.

The flutes and the grooves are oriented at opposite acute angles with respects to the longitudinal axis. Each flute defines a leading surface of a first one of the cutting edges and a trailing surface of a second, adjacent one of the cutting edges. The leading surface is oriented with respect to a radius of the cutting edge to define a positive rake for the cutting edge.

The notches provided in the cutting edges divide the cutting edges into relatively short, axially spaced segments. As a result, the cutting edges produce tissue fragments that are smaller than fragments that would be produced if the notches were not present. This is particularly useful when the burr is used to cut soft tissue, as the shorter cutting edge segments tend to chop up the soft tissue, rather than cutting long tissue strands that might become wound around the burr. The positive rake increases the sharpness of the cutting edges, thereby enabling the cutting edges to cut, rather than tear or shred, relatively soft tissue.

Other features and advantages will be apparent from the following detailed description and drawings, and from the claims.

DETAILED DESCRIPTION

Figure 1:
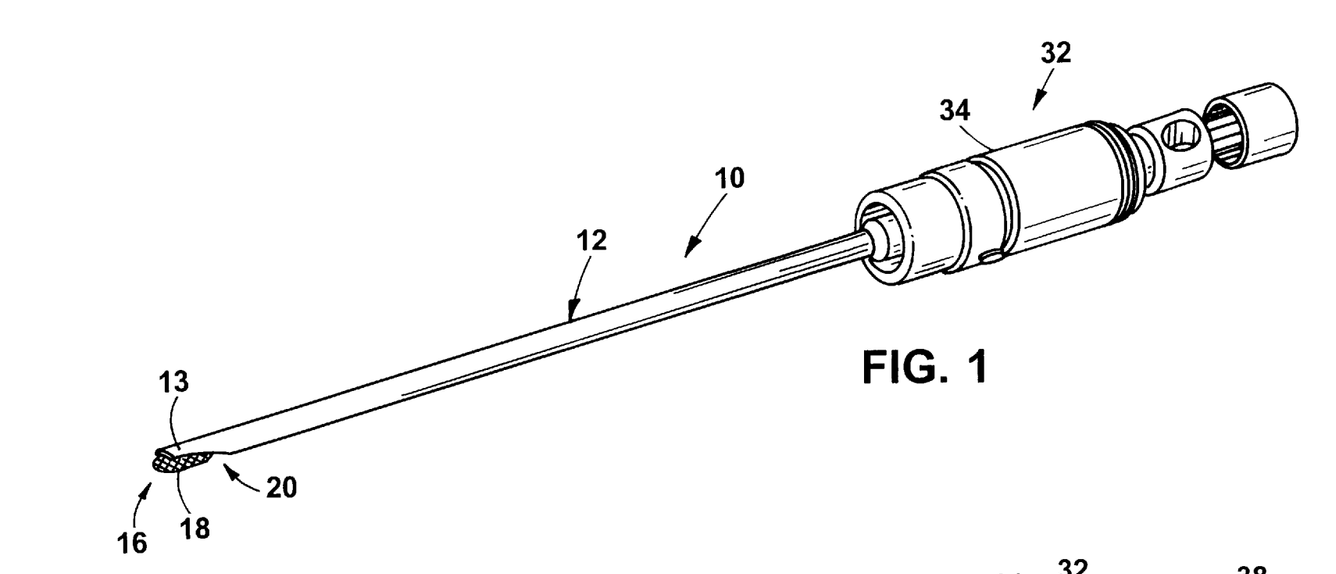
FIG. 1 is a perspective view of a surgical instrument.
Figure 2:
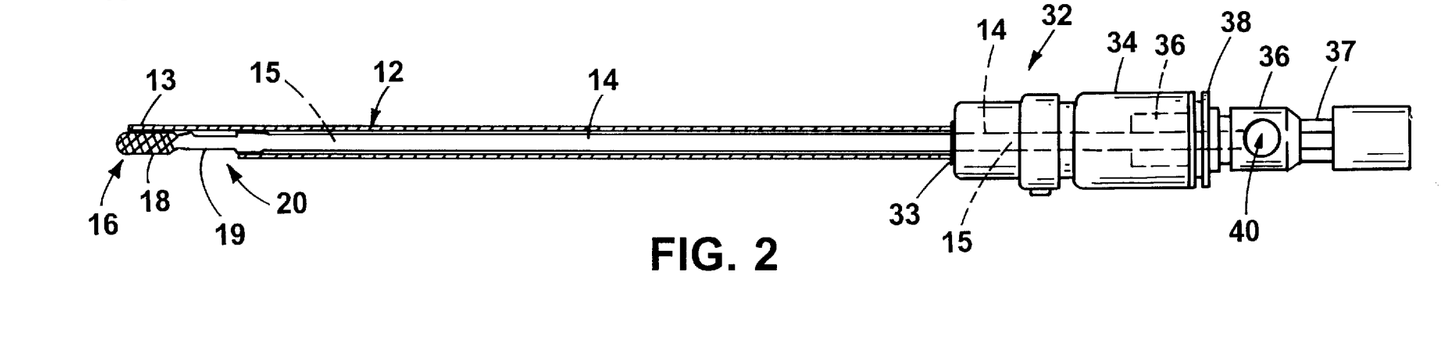
FIG. 2 is a side view, partially cut away, of the surgical instrument, showing an inner tube carrying a burr at its distal end disposed within an outer tube.
Figure 3:
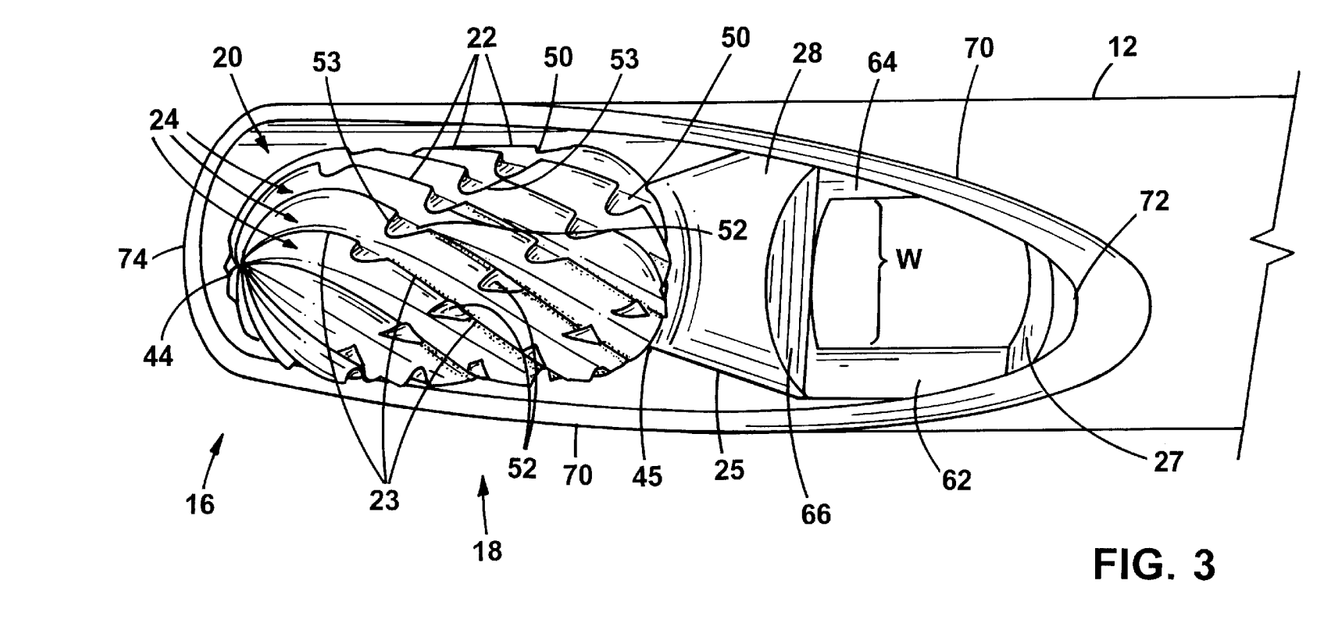
FIG. 3 is an enlarged, perspective view of the distal end of the surgical instrument, which shows the burr positioned within an axially elongated opening in the outer tube.

Referring to FIGS. 1–3, surgical instrument 10 includes a stationary outer tube 12 within which an inner tube 14 is rotatably disposed. A surgical tool 16 including a fluted burr 18 and a proximal shank 19 is mounted to a distal end of inner tube 14. Burr 18 is exposed to tissue through an opening 20 in the distal end of outer tube 12. As discussed in more detail below, the configuration of burr 18 renders it suitable for cutting both bone tissue and softer tissue (such as cartilage and synovial tissue).

Briefly, burr 18 includes a plurality of axially elongated, inclined sharpened cutting edges 22 circumferentially spaced from each other by correspondingly axially elongated, inclined flutes 24 disposed in an exterior surface of burr 18. Burr 18 is a solid distal extension of shank 19, which is tubular, and is connected to shank 19 by a tapered neck 25. A large aperture 26 in an exterior wall 28 of shank 19 intersects a cylindrical interior chamber 30 in shank 19 for admitting tissue fragments and irrigating fluid into chamber 30.

Inner tube 14 includes a suction passage 15 that communicates with chamber 30. During use, as inner tube 14 rotates, tissue exposed to burr 18 is cut by rotating cutting edges 22, and the resulting tissue fragments and irrigating fluid are conveyed through aperture 26 into chamber 30. Suction applied to passage 15 at the proximal end 32 of instrument 10 transports the tissue fragments and irrigating fluid proximally through inner tube 14 for removal from the body, while surgical instrument 10 remains in situ for further cutting.

Outer tube 12 is rigidly mounted to a hub 34 at proximal end 33. Hub 34 rotatably receives a base 36 to which the proximal end of inner tube 14 is attached. Base 36 is retained in hub 30 by a pliable fitting 38. Passage 15 terminates proximally in a suction port 40 in base 34. This construction is described, for example, in the above-discussed U.S. Pat. No. 5,322,505.

During use, proximal end 32 of instrument 10 is inserted into a handpiece 90 (shown in FIG. 9), which includes a motor 92 for engaging the proximal end 37 of base 36, which serves as a drive shaft for inner tube 14. Operation of the motor rotates inner tube 14 (and thus burr 18) within outer tube 12. (One example of such a handpiece is described in U.S. Pat. No. 4,705,038, assigned to the assignee of the present invention, and incorporated by reference herein.) Fitting 38 provides a fluid-tight seal with handpiece 90. As discussed below, handpiece 90 applies suction from an external vacuum source 96 to suction port 40 to withdraw the tissue fragments and irrigating fluid from inner tube 14.

Surgical instrument 10 is preferably disposable, that is, the device is made to be discarded after a single (or relatively few) uses. Outer tube 12 is made from stainless steel, while inner tube 14 is fabricated from softer, phosphor bronze (e.g., Alloy A UNS 51000) for purposes to be described. Hub 34 and base 36 are plastic. Other materials may be used instead if, e.g., surgical instrument 10 is to be autoclavable and reusable.

Figure 4:
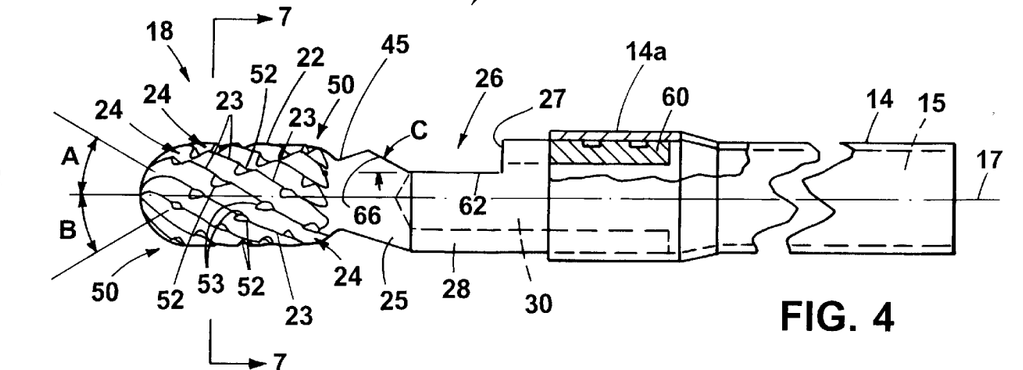
FIG. 4 is a side view, partially cut away, of the burr and the distal end of the inner tube.
Figure 5:
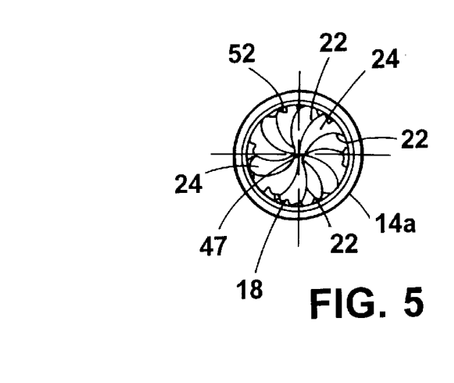
FIG. 5 is an end view of the burr of FIG. 4.

Surgical tool 16 is shown in detail in FIGS. 3–5. Cutting edges 22 of burr 18 are primarily constructed and arranged to cut relatively hard tissue such as bone, but as discussed below, the configuration of burr 18 enables cutting edges 22 to effectively cut softer tissue as well. Burr 18 and shank 19 comprise an integral unit made from a single member of stainless steel (e.g., Type S45500) and is hardened to a Rockwell hardness of at least 45. Cutting edges 22 are defined by a set of axially elongated flutes 24 formed (such as by machining) in the exterior surface of burr 18. Flutes 24 are inclined at an acute angle A (e.g., 30 degrees) with respect to a longitudinal axis 17 of surgical tool 16 and inner tube 14. As a result, cutting edges 22 are also axially elongated and inclined at acute angle A with respect to longitudinal axis 17. A total of twelve cutting edges 22 are distributed around the periphery of burr 18 and are equally circumferentially spaced from each other by flutes 24.

Cutting edges 22 extend axially from a generally hemispherical distal tip 44 of burr 18 to the junction 45 between burr 18 and neck 25. At distal tip 44, cutting edges 22 are oriented transversely to longitudinal axis 17 and extend radially from the center 47 of distal tip 44 to the periphery of burr 18. Slightly proximally of tip 44, cutting edges 22 curve helically and extend axially along the periphery of burr 18 at inclination angle A, discussed above.

A plurality of axially elongated grooves 50 are formed in burr 18 transversely to cutting edges 22 and flutes 24. Grooves 50 are inclined at an acute angle B with respect to longitudinal axis 17. Preferably, groove angle B is equal to, but oppositely directed from, flute angle A, and thus in this embodiment grooves 50 are oriented at −30 degrees with respect to longitudinal axis 17. Grooves 50 define a series of axially spaced, sharpened V-shaped notches 52 in cutting edges 22. Notches 52 are cut relatively deeply into cutting edges 22; for example, notches 52 are 80% of the depth of flutes 24. Notches 52 interrupt each cutting edge 22, dividing it into a series of shorter, axially spaced segments 23 each of which includes a sharpened, transverse cutting surface 53 defined by an edge of a notch 52. The shorter segments 23 produce correspondingly smaller tissue fragments for easier aspiration from the surgical site without clogging aperture 26, chamber 30, or passage 15.

For example, when bone tissue is being cut by burr 18, the bone fragments produced by cutting edge segments 23 are smaller then they would be if notches 52 were not present, thereby allowing the fragments to more easily pass into suction passage 15 via aperture 26 and chamber 30. In addition, when burr 18 is used on softer tissue, the sharpened edges 53 of notches 52 cause cutting edge segments 23 to chop up the tissue into small pieces (rather than longer strips, as could be produced in cutting edges 22 were not interrupted by notches 52). As a result, the tendency of the severed tissue to wrap around and become caught on burr 18 is reduced, and the smaller pieces of tissue are easily conveyed through shank aperture 26 and chamber 30 and into suction passage 15.

The risk of clogging is further reduced by the relatively large size of aperture 26 and the cylindrical configuration of chamber 30. That is, unlike conventional burrs which include a long, narrow slot (e.g., 0.075 inches in width) in the shank for conveying bone fragments into the inner tube suction passage, aperture 26 has a substantial width and opens into an even larger cylindrical chamber 30. Preferably, the width W of aperture 26 is at least one-half of, and more preferably greater than one-half of, the diameter of wall 28. For example, aperture 26 has a width W of approximately 0.135 inches, while the outer diameter of wall 28 is about 0.22 inches. Aperture 26 is approximately 0.210 inches long, and is thus much less oblong than the slots found in conventional burr shanks. Chamber 30 has a diameter of between 0.140 inches and 0.150 inches, and extends proximally from aperture 26 to the proximal end 60 of shank 19. Chamber 30 thus readily accommodates even large tissue fragments conveyed through aperture 26.

As shown in FIGS. 3 and 4, the sides of aperture 26 are defined by a pair of flat axial surfaces 62, 64 that lie in a common plane recessed from the exterior surface of wall 28 and parallel to longitudinal axis 17. A flat, inclined surface 66 is formed in wall 28 at the distal end of aperture 28. Surface 66 slopes proximally toward aperture 26 from neck 25, and meets the plane defined by surfaces 62, 64 at the distal end of aperture 26. The angle C between surface 66 and the plane of surfaces 62, 64 is preferably shallow, such as approximately 30 degrees. As a result, surface 66 serves as a ramp which guides tissue fragments cut by burr 18 past neck 25 and into aperture 26.

Figure 6:
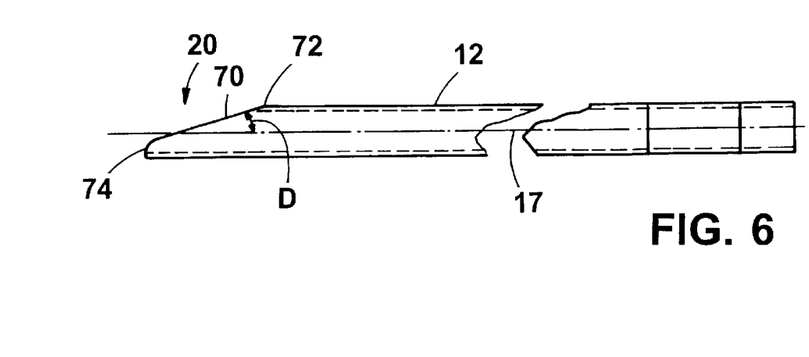
FIG. 6 is a side view of the outer tube of the surgical instrument.

Referring to FIGS. 3 and 6, outer tube opening 20 is sufficiently axially elongated to expose substantially all of aperture 26. Thus, unlike typical abrading instruments, in which the majority of the tissue-admitting opening in the burr shank (i.e., the slot) is covered by the outer tube, substantially the entire length of aperture 26 is exposed by opening 20. This, combined with the increased size of aperture 26, significantly improves the flow path for the irrigation fluid and tissue fragments aspirated into inner tube passage 15, thereby dramatically increasing the efficiency at which the severed tissue fragments are aspirated through inner tube 14.

More specifically, the increased axial elongation of outer tube opening 20 is provided by decreasing the angle defined between the edges 70 of opening 20 and longitudinal axis 17. Edges 70 are flat and define an entrance plane for opening 20 which is oriented at a relatively shallow angle D, for example, approximately 15 degrees, to longitudinal axis 17. As a result, opening 20 is substantially longer than outer tube openings of typical abrading instruments (the edges of such openings are generally oriented at a relatively large angle, such as 25 degrees, to the longitudinal axis). As a result, outer tube opening 20 is "laid back" so that its proximal end 72 is positioned adjacent to—and preferably proximally of—the proximal end 27 of aperture 26 (FIG. 3). Put another way, proximal end 72 of opening 20 is located well behind (such as by 0.8 inches) the distal tip of outer tube 12.

At the distal tip of outer tube 12, the edges 70 of opening 20 are rounded to meet a distal transverse edge 74. Edge 74 is blunt and preferably is positioned slightly proximally of distal tip 44 of burr 18. This allows burr distal tip 44 to be used for end-on cutting, if desired. The axial elongation of opening 20 defines a distal portion of outer tube 12 which serves as a hood 13 for one side of burr 18. Put another way, hood 13 partially surrounds one side of burr 18, to protect adjacent tissue from the cutting action of burr 18, while also exposing the opposite side (and distal tip 44) of burr 18 to the tissue that the surgeon desires to cut.

Figure 7:
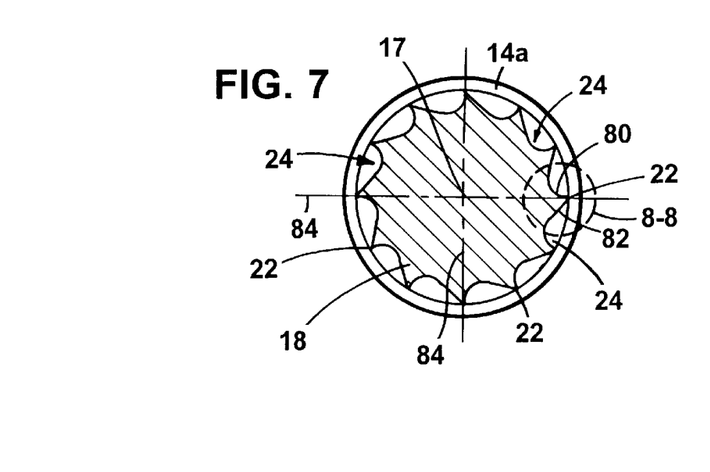
FIG. 7 is a cross-sectional view of the burr, taken along line 7—7 of FIG. 4.
Figure 8:
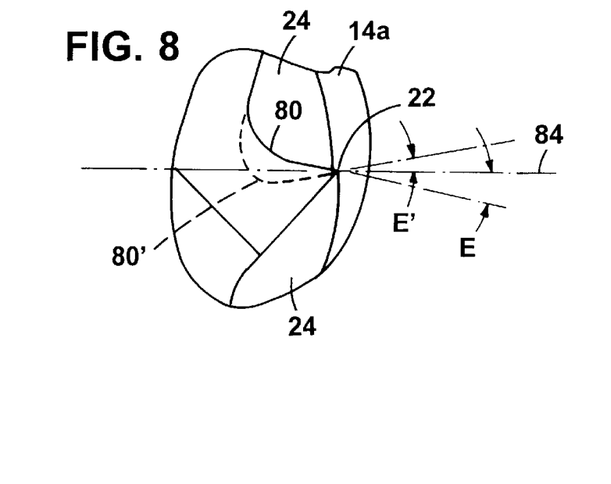
FIG. 8 is an enlarged view of one of the cutting edges of the burr located within circle 8—8 of FIG. 7.

Referring to FIGS. 7 and 8, cutting edges 22 are configured to enable burr 18 to effectively cut soft tissue as well as harder tissue such as bone. One aspect of this construction—notches 52, which break up the cutting action of edges 22—is discussed above. Another feature is that the so-called "rake" of cutting edges 22 is made to be neutral to slightly positive, rather than highly negative as in conventional burrs.

The rake of a cutting edge is defined by the angle between the leading surface of the cutting edge (that is, the surface that first impacts the tissue during rotation of the burr) and the radius of the burr. Each cutting edge 22 is defined by a leading surface 80 from one flute 24 and a trailing surface 82 from an adjacent flute 24. Leading surface 80 defines an angle E with the radius 84 of the cutting edge 22. (Radius 84 is formed by a line which extends from the center of burr 18 on longitudinal axis 17 through cutting edge 22 at the periphery of burr 18.) As shown in FIG. 8, angle E is slightly negative (i.e., below radius 84), for example, between 5 degrees and 10 degrees. As a result, the cutting edge 22 shown in FIG. 8 has a slightly negative rake.

Preferably, however, flutes 24 are undercut further during fabrication to define leading surfaces 80' that lie on or below radius 84. In this case, the angle E' defined by surface 80' is zero to slightly positive (by, e.g., a few degrees), and as a result cutting edges 22 have a neutral to slightly positive rake. When cutting edges 22 are made having this configuration, edges 22 are sharper than they would be if they had a negative rake. Accordingly, fabricating cutting edges 22 in this fashion renders edges 22 suitable for efficiently cutting (rather than tearing or shredding) relatively soft tissue.

Surgical tool 16 is manufactured from a cylindrical, stainless steel blank with a hemispherical tip as follows. First, shank 19 and neck 25 (FIG. 3) are machined at the proximal end of the blank, and chamber 30 is drilled out. Then, the blank is heat treated to harden it to the required Rockwell hardness. Twelve flutes 24 are then machined by grinding to define cutting edges 22 at the desired neutral to slightly positive rake discussed above. Next, the blank is repositioned in the grinding machine, and six grooves 50 are ground to define notches 52 in cutting edges 22.

Aperture 26 is cut into shank walls 28 by electric discharge machining (EDM). The EDM cutting wire first cuts inclined surface 66 at the selected acute angle, then proceeds distally parallel to axis 17, and finally makes a perpendicular cut to define proximal end 27 of aperture 26.

Referring again to FIG. 4, during assembly of instrument 10, proximal end 60 of burr shank 19 is inserted into a distal end 14a of inner tube 14, which is enlarged to accept shank 19. Proximal end 60 of shank 19 is secured within the distal end 14a of inner tube 14 swaging; a pair of circumferential grooves 61 are provided in shank 19 for this purpose. Other, alternative techniques for attaching shank 19 to inner tube 14 include spot, laser or electron beam welding, brazing, or gluing.

The assembled inner tube 14 is inserted through hub 34 into outer tube 12 until base 36 becomes seated within hub 34 (FIG. 1). The outer diameter of inner tube 14 is significantly less than the inner diameter of outer tube 12 to provide clearance between tubes 12, 14. The outer diameter of inner tube distal end 14a is, however, only slightly smaller than the inner diameter of outer tube 12 so that distal end 14a serves as a bearing for burr 18 against side loads. A heat-shrunk plastic sleeve (not shown) having approximately the same outer diameter as distal end 14a is provided around inner tube 14 near its proximal end to provide a proximal bearing surface against outer tube 12.

Figure 9:
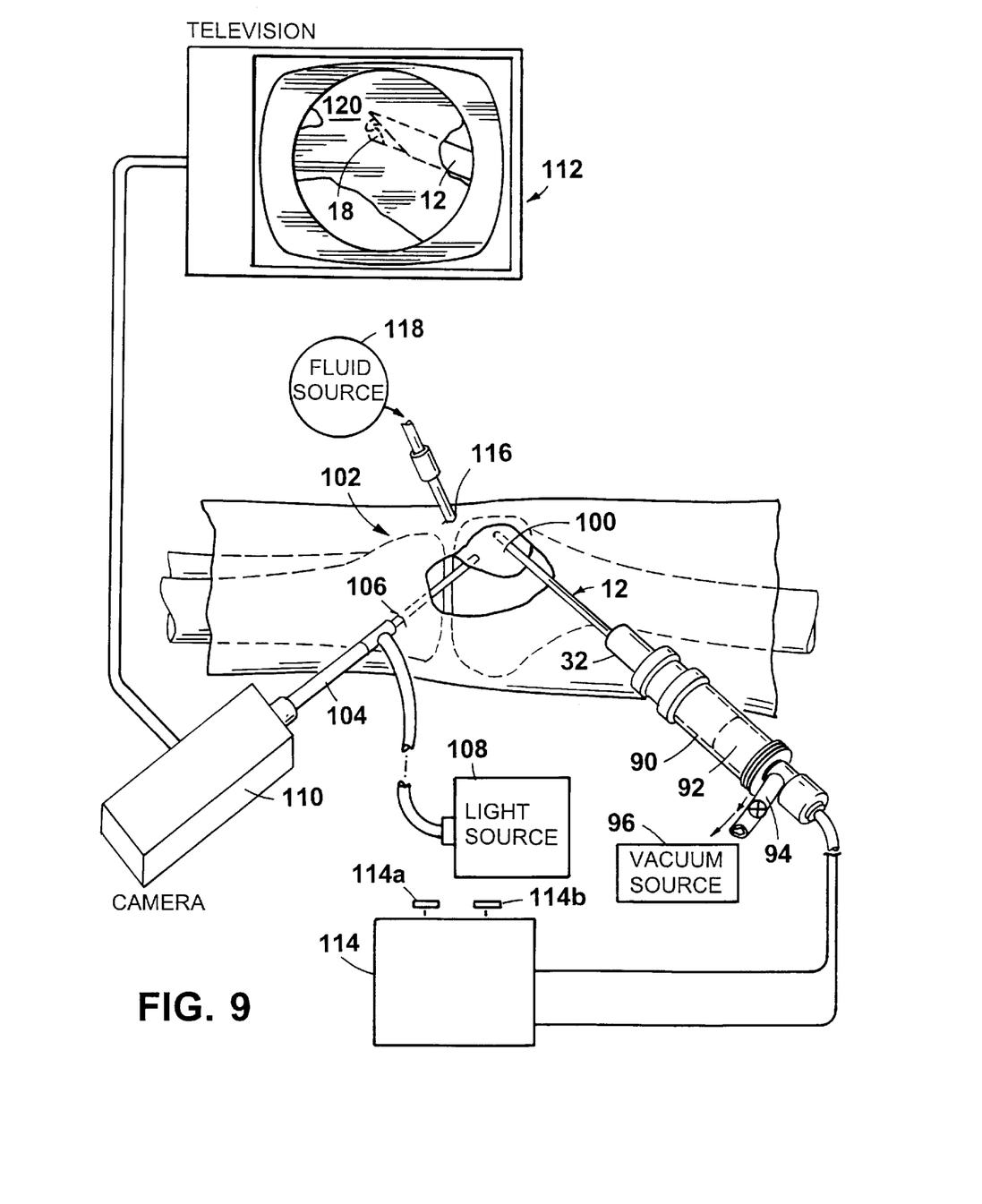
FIG. 9 shows the surgical instrument in use.

Referring to FIG. 9, in use, surgical instrument 10 is inserted into the distal end of handpiece 90. As discussed above, handpiece 90 includes a motor 92 for engaging proximal end 37 of base 36 to rotate inner tube 14. Handpiece 90 also includes a vacuum fitting 94 through which suction from a vacuum source 96 is applied to suction port 40 (FIG. 2) of instrument 10.

The distal end of surgical instrument 10 is introduced through a puncture wound 100 into a patient's knee joint 102, below the patella. An endoscope 104 inserted into joint 102 through a second puncture 106 both provides illumination (from light source 108) to the surgical site and conveys an image of the surgical site to a television camera 110. The image is delivered by camera 110 to a television screen 112 for viewing by the surgeon. Alternatively, the surgeon may view the image using an eyepiece on endoscope 104, or the image may be recorded.

Joint 102 is inflated with fluid introduced through a third puncture wound 116 from a fluid source 118. The fluid irrigates the surgical site and provides a medium by which tissue fragments cut by burr 18 are drawn through aperture 26, into chamber 30, and thence into tube passage 15 by the suction applied by vacuum source 96.

The surgeon maneuvers the distal end of instrument 10 to urge burr 18 (exposed by outer tube opening 20) against the tissue 120 (e.g., a section of bone or softer tissue such as synovial tissue or cartilage) to be cut. The surgeon then activates motor 92 to rotate inner tube 14 and surgical tool 16. Motor 92 receives operating potential and current from power supply 114. The surgeon controls the rotational speed and direction (either unidirectional or oscillatory, although an abrader such as surgical tool 16 is typically operated in one direction only) using foot switches 114a, 114b, which control the magnitude and polarity of operating potential and current supplied by power supply 114 to motor 92. Motor 92 is capable of rotating inner tube 14 over a wide range of speeds, e.g., between 100 rpm and 5000 rpm, and can deliver a torque of up to 25 oz inches.

When abrading bone tissue 120, cutting edges 22 of burr 18 abrade the bone as tool rotates. When cutting softer tissue 120, on the other hand, the enhanced sharpness provided by the neutral to slightly positive rake allows cutting edges 22 to efficiently cut (rather than tear or sever) the tissue during rotation of burr 18. The aggressiveness of the abrading/cutting action is a function of the speed of rotation and the pressure applied to tissue 120 by the surgeon. The surgeon progressively cuts tissue 120 by moving instrument 10 from side to side and axially, while viewing the surgical site on television screen 112.

Tissue fragments cut by burr 18 are broken or chopped up by the relatively short segments 23 of cutting edges 22, and are urged proximally by the rotation of fluted burr 18 and the irrigation fluid being drawn into aperture 26. The tissue fragments pass over neck 25 and inclined surface 66 and enter aperture 26 and chamber 30 along with the irrigation fluid. Inclined surface 66 acts as a ramp which guides the fragments into aperture 26, further reducing the risk of clogging. The fragments and irrigation fluid are then drawn into inner tube passage 15, are transported proximally through inner tube 14, and exit surgical instrument 10 at suction port 40.

Due to the large size of aperture 26 and its substantially complete exposure to the surgical site by outer tube opening 20, the tissue fragment and irrigation fluid flow rate supported by instrument 10 is increased by as much as 30% over conventional burr-equipped instruments. This substantially reduces the risk that instrument 10 will become clogged by the tissue fragments. The notched configuration of cutting edges 22 helps ensure that the tissue fragments are relatively small, further reducing chances of clogging. In addition, the rake of cutting edges 22 enables burr 18 to efficiently cut even soft tissue into small fragments that are easily carried into chamber 30 via aperture 26.

Enlarged distal end 14a of inner tube 14 serves as a bearing to maintain the rotating inner tube 14 and burr 18 spaced from the inner surface of outer tube 12. Because distal end 14a is located immediately proximally of cutting surfaces 22, distal end 14a provides proximal support for burr 18 against even relatively large side loads imposed when the surgeon urges burr against hard tissue 120 such as bone. This helps prevent burr 18 from contacting the inner surface of outer tube 12, thereby reducing wear of surgical tool 16 and avoiding "shedding" of steel fragments. The excellent bearing characteristics of the phosphor-bronze material of inner tube 14 also contributes to reduced shedding and helps reduce the risk of seizing (even at the high rotational speeds, e.g., 5000 rpm, at which burrs are typically operated) without need to coat the interior surface of outer tube 12 with a soft, precious metal (such as silver).

After use, surgical instrument 10 is cleaned if it is to be reused. The large size of apertures 26 and its exposure by outer tube opening 20 renders aperture 25 (and thus chamber 30) readily accessible for cleaning, without having to remove inner tube 14 from outer tube 12.

Other embodiments are within the following claims.

For example, additional apertures may be provided in shank 19 to increase fluid flow rate even further. The shape of aperture 26 and the size of outer tube opening 20 can be adjusted.

Burr may be provided with more or fewer cutting edges 22, flutes 24, and grooves 50, as desired. In general, the number of cutting edges 22 is a function of the diameter of burr 18 and the desired aggressiveness of the cutting action. More or fewer grooves 50 than are shown in FIGS. 3 and 4 may also be provided, as desired, according to burr 18 diameter. Notches 52 need not be disposed in every cutting edge 22.

Surgical tool 16 can have other "burr" shapes, if desired. Examples include tapered, oval, and round burrs.

Other cutting edge configurations are possible, depending upon the surgical application. In particular, cutting edges 22 can be helical to a greater or lesser extent than shown in FIGS. 3–5. Cutting edges 22 may also define other inclination angles with respect to longitudinal axis 40 (as may grooves 50). The rake of cutting edges 22 may be changed depending on the type of tissue to be cut.

Distal tip 44 of burr 18 may be configured in other ways. For example, tip 44 may be blunt so that no end-on cutting action takes place. Alternatively, tip 44 may be configured for even more aggressive end-on cutting. Also, tip 44 need not be hemispherical. Possible alternative shapes include square, conical, convex, and concave.

Although the use of instrument 10 has been explained with reference to knee surgery, it will be understood that instrument 10 can be employed in other endoscopic and arthroscopic procedures.

Still other embodiments are within the scope of the claims.

What is claimed is:

1. A surgical instrument comprising
   an outer tube having an opening at a distal end thereof,
   an inner tube disposed for rotation within said outer tube, said inner tube having an interior passage between a distal end and a proximal end thereof, and
   a surgical tool including a proximal shank mounted to said distal end of said inner tube and a fluted tissue cutting burr disposed distally of said shank and positioned within said outer tube opening, said shank including a wall that defines an interior chamber in communication with said passage, said wall including an aperture therein, a portion of said wall disposed adjacent to a distal end of said aperture and including an inclined surface that slopes proximally toward said aperture, said wall including a pair of axial surfaces that define sides of said opening that are disposed in a plane, said inclined surface being oriented at an acute angle with respect to said plane, said aperture intersecting said chamber for conveying tissue fragments cut by said burr into said chamber and thence into said passage, said aperture having a substantial width relative to an outer diameter of said wall.

2. The surgical instrument of claim 1 wherein the width of said aperture is approximately one-half of said outer diameter of said wall.

3. The surgical instrument of claim 1 wherein the width of said aperture is greater than one-half of said outer diameter of said wall.

4. The surgical instrument of claim 1 wherein said wall of said shank is tubular so that said interior chamber is substantially cylindrical.

5. The surgical instrument of claim 1 wherein said outer tube opening is axially elongated between a distal end at said distal end of said outer tube and a proximal end disposed proximally of said burr, thereby to expose said burr along one side of said outer tube and define a portion of said outer tube that provides a hood for an opposite side of said burr.

6. The surgical instrument of claim 5 wherein said outer tube opening is axially elongated sufficiently to expose a major portion of said aperture.

7. The surgical instrument of claim 5 wherein said outer tube opening is axially elongated so that said proximal end of said opening is disposed adjacent to a proximal end of said aperture.

8. The surgical instrument of claim 7 wherein said outer tube opening is axially elongated so that said proximal end of said opening is disposed proximally of said proximal end of said aperture.

9. The surgical instrument of claim 1 wherein said burr includes a plurality of cutting edges circumferentially spaced by a plurality of flutes disposed in an exterior surface of said surgical tool for cutting tissue exposed to said burr by said opening in said outer tube during rotation of said inner tube.

10. The surgical instrument of claim 9 wherein at least one of said cutting edges includes at least one notch therein.

11. The surgical instrument of claim 9 wherein said cutting edge includes a plurality of axially spaced notches therein.

12. The surgical instrument of claim 9 wherein each one of said cutting edges includes a plurality of axially spaced notches therein.

13. The surgical instrument of claim 9 wherein said cutting edges and said flutes are axially elongated and inclined relative to a longitudinal axis of said burr.

14. The surgical instrument of claim 13 wherein said burr further comprises a plurality of grooves that are axially elongated and inclined transversely to said flutes, said grooves defining a plurality of axially spaced notches in each of said cutting edges.

15. The surgical instrument of claim 14 wherein said flutes and said grooves are oriented at opposite acute angles with respect to said longitudinal axis.

16. The surgical instrument of claim 9 wherein each one of said flutes defines a leading surface of a first one of said cutting edges and a trailing surface of a second, adjacent one of said cutting edges.

17. The surgical instrument of claim 16 wherein said leading surface is oriented with respect to a radius of said cutting edge to define a positive rake for said cutting edge.

18. A surgical instrument comprising an outer tube, an inner tube disposed for rotation within said outer tube, said inner tube having an interior passage between a distal end and a proximal end thereof, and a surgical tool including a proximal shank mounted to said distal end of said inner tube and a fluted tissue cutting burr disposed distally of said shank, said shank including a wall that defines an interior chamber in communication with said passage, said wall including an aperture therein and a portion disposed adjacent to a distal end of said aperture, said wall portion including an inclined surface that slopes proximally toward said aperture, said wall including a pair of axial surfaces that define sides of said opening that are disposed in a plane, said inclined surface being oriented at an acute angle with respect to said plane, said aperture intersecting said chamber for conveying tissue fragments cut by said burr into said chamber and thence into said passage, said outer tube including an axially elongated opening at a distal end thereof to expose said burr along a side of said outer tube, said opening being sufficiently axially elongated to expose a major portion of said aperture.

19. The surgical instrument of claim 18 wherein said outer tube opening is axially elongated so that a proximal end of said opening is disposed adjacent to a proximal end of said aperture.

20. The surgical instrument of claim 19 wherein said outer tube opening is axially elongated so that said proximal end of said opening is disposed proximally of said proximal end of said aperture.

21. The surgical instrument of claim 18 wherein said aperture has a substantial width relative to an outer diameter of said wall.

22. The surgical instrument of claim 21 wherein the width of said aperture approximately one-half of said outer diameter of said wall.

23. The surgical instrument of claim 21 wherein the width of said aperture is greater than one-half of said outer diameter of said wall.

24. The surgical instrument of claim 18 wherein said burr includes a plurality of axially elongated cutting edges circumferentially spaced by a plurality of flutes disposed in an exterior surface of said surgical tool for cutting tissue exposed to said burr by said opening in said outer tube during rotation of said inner tube, said cutting edges and said flutes being axially elongated and inclined relative to a longitudinal axis of said burr, and a plurality of grooves that are axially elongated and inclined transversely to said flutes, said grooves defining a plurality of axially spaced notches in each of said cutting edges.

25. The surgical instrument of claim 24 wherein said flutes and said grooves are oriented at opposite acute angles with respect to said longitudinal axis.

26. The surgical instrument of claim 24 wherein each one of said flutes defines a leading surface of a first one of said cutting edges and a trailing surface of a second, adjacent one of said cutting edges, said leading surface being oriented with respect to a radius of said cutting edge to define a positive rake for said cutting edge.

27. A surgical instrument comprising an outer tube having an opening at a distal end thereof, an inner tube disposed for rotation within said outer tube, said inner tube having an interior passage between a distal end and a proximal end thereof, and a surgical tool including a proximal shank mounted to said distal end of said inner tube and a fluted tissue cutting burr disposed distally of said shank and positioned within said outer tube opening, said burr including: (1) a plurality of axially elongated cutting edges circumferentially spaced by a plurality of flutes disposed in an exterior surface of said surgical tool for cutting tissue exposed to said burr by said opening in said outer tube during rotation of said inner tube, said cutting edges and said flutes being axially elongated and inclined relative to a longitudinal axis of said burr, and (2) a plurality of grooves that are axially elongated and inclined transversely to said flutes, said grooves defining a plurality of axially spaced notches in each of said cutting edges, said shank including a wall that defines an interior chamber in communication with said passage, said wall having an outer diameter and including an aperture therein and a portion disposed adjacent to a distal end of said aperture, said wall portion including an inclined surface that slopes proximally toward said aperture, said wall including a pair of axial surfaces that define sides of said opening that are disposed in a plane, said inclined surface being oriented at an acute angle with respect to said plane, said aperture intersecting said chamber for conveying tissue fragments cut by said burr into said chamber and thence into said passage, said aperture having a substantial width relative to said outer diameter of said wall, said outer tube opening being axially elongated to expose said burr along a side of said outer tube, said opening being sufficiently elongated to expose a major portion of said aperture.

* * * * *